US007122380B1

(12) United States Patent
Jacquemin et al.

(10) Patent No.: US 7,122,380 B1
(45) Date of Patent: Oct. 17, 2006

(54) PHARMACEUTICAL COMPOSITIONS CONTAINING ANTIGEN-ANTIBODY COMPLEXES AND USES THEREFOR

(75) Inventors: Marc Jacquemin, Waremme (BE); Jean-Marie St. Remy, Grez Doiceau (BE); Philippe Lebrun, Vieusart (BE); Serge Lebecque, Gembloux (BE); Piere Masson, Brussels (BE)

(73) Assignee: International Institute of Cellular and Molecular Pathology, Brussels (BE)

( * ) Notice: Subject to any disclaimer, the term of this patent is extended or adjusted under 35 U.S.C. 154(b) by 0 days.

(21) Appl. No.: 08/242,076

(22) Filed: May 13, 1994

Related U.S. Application Data

(63) Continuation of application No. 07/806,772, filed on Dec. 11, 1991, now abandoned, which is a continuation of application No. 07/460,514, filed on Jan. 3, 1990, now abandoned, which is a continuation-in-part of application No. 07/038,985, filed on Apr. 16, 1987, now abandoned, which is a continuation-in-part of application No. 06/651,073, filed on Sep. 17, 1984, now Pat. No. 4,740,371.

(51) Int. Cl.
*G01N 33/564* (2006.01)
(52) U.S. Cl. .................................................... 436/507
(58) Field of Classification Search ............... 424/85.8, 424/88, 141.1, 172.1, 184.1, 193.1; 514/2, 514/8, 12, 21, 44; 530/350, 387, 388, 395, 530/387.1, 388.1, 388.15, 388.22, 389.1, 530/388.21; 435/70.21, 172.2, 240.27; 536/23.1; 436/507
See application file for complete search history.

(56) References Cited

U.S. PATENT DOCUMENTS

| 4,140,679 A | 2/1979 | Malley ........................ 424/88 |
| 4,234,569 A | 11/1980 | Marsh ........................ 424/91 |
| 4,344,938 A | 8/1982 | Sedlacek et al. ............ 424/177 |
| 4,521,405 A | 6/1985 | McMichael |
| 4,545,986 A | 10/1985 | Malley ........................ 424/91 |
| 4,564,600 A | 1/1986 | Ali et al. .................... 436/513 |
| 4,681,760 A | 7/1987 | Fathman et al. .............. 424/85 |
| 4,702,907 A | 10/1987 | Becker et al. ................ 424/88 |
| 4,714,759 A | 12/1987 | Whitaker, Jr. |

FOREIGN PATENT DOCUMENTS

| EP | 0217577 | 4/1987 |
| EP | 0240344 | 10/1987 |
| EP | 0245078 | 11/1987 |

OTHER PUBLICATIONS

Schwartz, R.S., "Autoimmunity and Autoimmune Diseases" in *Fundamental Immunology*, 3rd Ed., Paul, W.E., Ed., Raven Press, New York, pp. 1069-1074, 1993.*
Brostoff et al., *Clinical Immunology*, Gower Medical Publishing, New York, pp. 6.1-6.14, 1991.*
Putterman et al, "Murine Models of Spontaneous Sytomic Lupus Erythematasus," in *Autoimmune Disease Models: A Guidebook*, Academic Press, San Diego, pp. 217-243, 1994.*
Barkas et al., J. Clin. Lab Immunol. 7 (1982) p. 223.
Borel et al., J. Clin. Investigation 82 (1988) p. 1901.
Borel et al., Ann. N.Y. Acad. Sci. 476 (1986) p. 296.
Borel et al., J. of Immunological Methods 126 (1990) p. 159.
Caulfield et al., J. Immunology 138 (1987) p. 3680.
Farkas et al. Immunology 45 (1982) p. 483.
Klaus, Nature 272 (1978) p. 265.
Klaus, Immunology 37 (1979) p. 345.
Klaus, Nature 278 (1979) p. 354.
G. G. B. Klaus, "Antigen-antibody Complexes Elicit Anti-Idiotypic Antibodies to Self-Idiotopes," *Nature*, vol. 272, pp. 265-266, Mar. 16, 1978.
A. I. Farkas, et al, "Immunogenicity of Antigen Complex With Antibody," *Immunology*, vol. 45, pp. 483-492, 1982.
Klaus, "Cooperation Between Antigen-Reactive T Cells and Anti-Idiotypic B Cells in the Anti-Idiotypic Response . . . " 278 Nature 354 (Mar. 22, 1979).
Roitt, I. et al., *Immunology*, C.V. Mosby Co., St. Louis (1985) pp. 21.1-21.10.
Barkas, T. et al., "Preliminary Communication Experimental Myasthenia Gravis is Inhibited by Receptor-Antireceptor Complexes", *J. Clin. Lab. Immunol.*, vol. 7 (1982), pp. 223-227.
Borel, H. et al., "A Possible New Therapy of Systemic Lupus Erythematosus (SLE)$^a$", *Ann. N.Y. Acad. Sci.*, vol. 476 (1986) pp. 296-305.
Caulfield, M.J. et al., "Immunoregulation by Antigen/Antibody Complexes I. Specific Immunosuppression Induced in Vivo with Immune Complexes Formed in Antibody Excess", *Journal of Immunology*, vol. 138 (1987), pp. 3689-3683.

(Continued)

*Primary Examiner*—Bruce R. Campell
*Assistant Examiner*—Agnieszka Boesen
(74) *Attorney, Agent, or Firm*—Venable LLP; Clifton E. McCann

(57) ABSTRACT

A pharmaceutical composition suitable for administration to human beings in the prevention or treatment of immunologic disorders includes:

an immune complex of an antigen and a purified antibody specific thereto, the antigen being selected from a group consisting of antigens that cause pathogenic immunologic reactions in autoimmune disease and graft rejections, and the antigen and antibody being present in a ratio whereby the antibody blocks essentially all binding sites of the antigen; and a pharmacologically acceptable carrier or diluent.

The invention also provides a method of administering the composition for treatment of autoimmune disease and treatment or prevention of graft rejections.

31 Claims, No Drawings

OTHER PUBLICATIONS

Borel, Y. et al., "Oligonucleotide Linked to Human Gammaglobulin Specifically Diminishes Anti-DNA Antibody Formation in Cultured Lymphoid Cells from Patients with Systemic Lupus Erythematosus", *J. Clin Invest.*, vol. 82 (1988), pp. 1901-1907.

Borel, H. et al., "A novel technique to link either proteins or peptides to gammaglobulin to construct tolerogens", *Journal of Immunological Methods*, vol. 126 (1990) pp. 159-168.

Caulfield, M., "Idiotype-Restricted Antibody Response to Specific Immune Complexes", *Cellular Immunology*, vol. 90 (1985), pp. 451-437.

Caulfield, M. et al., "The Antibody Response to Specific Immune Complexes is Under Genetic Control and Correlates with the Expression of a Recurrent Idiotype", *J. Exp. Med.*, vol. 163 (1986), pp. 75-86.

Filion, L.G. et al., "Suppression of the IgE Antibody Response to Ovalbumin in Mice with a Conjugate of Ovalbumin and Isologous γ-Globulins", *Cellular Immunology*, vol. 54 (1980), pp. 115-128.

Lee, W.Y. et al. "Suppression of Reaginic Antibody Formation I. Introduction of Hapten-Specific Tolerance", *The Journal of Immunology*, vol. 114, No. 2, Part 2 (1975), pp. 829-836.

Lee, W.Y. et al., "Tolerization of Bε Cells by Conjugates of Haptens and Isologous γ-Globulins", *Cellular Immunology*, vol. 58, (1981), pp. 385-397.

Seropian, E. et al., "'Alergim'—Blocking Antibody IgG Specific in Intraseasonal Treatments of Pollenosis: Clinical Results", *Imunolgie XIII*, Academia De Stiinte Medicale Comisia Nationala De Imunologie Subcomisia Tirgu Mures.

Seropian, E. et al., "'ALERGIM', A Specific Immune Complex for the Intraseasonal Treatment of Pollinosis. A Clinical Trial", *Abstracts Interlaken 1984—6th European Immunology Meeting*, (1984), p. 325.

Uhr, J.W. et al., "Regulatory Effect of Antibody on the Immune Response", *Advances in Immunology* vol. 8, (1968) pp. 81-127.

Andrew F. Geczy, et al, "Suppression of Reaginic Antibody Formation in Guinea Pigs by Anti-idiotypic Antibodies," *J. Allergy Clin Immunol*, vol. 62(5): 261-270, 1978.

Kurt Blaser, et al, "Suppression of Phosphorylcholine-Specific IgE Antibody Formation in BALB/c Mice by Isologous Anti-T 15 Antiserum," Eur. J. Immunol. 1979.9:1017-1020.

Kurt Blaser, et al, "Suppression of the Benzylpenicilloyl-(BPO) Specific IgE Formation With Isologous Anti-Idiotypic Anti-bodies in BALB/c Mice," *The Journal of Immunology*, vol. 125, No. 1, pp. 24-30, Jul. 1980.

K. Blaser, et al, "Investigation of a Syngeneic Murine Model for the Study of IgE Antibody Regulation With Isologous, Antiidiotypic Antibodies," *Int. Archs Allergy Appl. Immun.* 64: 42-50 (1981).

Raif S. Geha, M.D., "Current Concepts in Immunology," *The New England Journal of Medicine*, vol. 305, No. 1, pp. 25-28, Jul. 2, 1981.

A. I. Farkas, et al, "Immunogenicity of Antigen Complex With Antibody," *Immunology*, vol. 45, pp. 483-492, 1982.

Raif S. Geha & Marc Comunale, "Regulation of Immunoglobulin E Antibody Synthesis in Man by Antiidiotypic Antibodies," *J. Clin. Invest.*, vol. 71, pp. 46-54, Jan. 1983.

Paul D. Buisseret, "Allergy," *Scientific American*, pp. 82-91, Aug. 1982.

Howard J. Sanders, "Allergy, A Protective Mechanism Out of Control," *Chemical & Engineering News*, vol. 48, pp. 84-135, May 11, 1970.

"Primer on Allergic and Immunologic Diseases," *Journal of the American Medical Association*, vol. 248, No. 20, Nov. 26, 1982.

Arend et al, "In Vitro Adherence of Soluble Immune Complexes to Macrophages", 136 J. Exp. Med. 514 (1972).

Klaus, "Generation of Memory Cells, III. Antibody Class Requirements for the Generation of B-Memory Cells by Antigen-Antibody . . . " 37 Immunology 345 (1979.

Caulfield et al, "Induction of Idiotype-Specific Suppressor T Cell with Antigen/Antibody Complexes", 157 J. Exp. Med. 1713 (1983).

Blaser et al, "Immune Networks in Immediate Type Allergic Diseases", 418 Ann. NY Acad. Sci . 330 (1983).

Blaser et al, "Regulation of the IgE Antibody Response by Idiotype-Anti-Idiotype Network", 32 Prog. Allergy 203 (1982).

Blaser et al, "Regulatory Effects of Isoloqous Anti-idiotypic Antibodies on the Formation of . . . ", 14 Eur. J. Immunol. 93-98 (1984) 50 Fed. Reg. 3082 (Jan. 23, 1985).

Glover, D.M., *Gene Cloning: The Mechanics of DNA Manipulation*, pp. 102-104, Chapman and Hall, London (1984).

Lee, W.Y. et al., "Suppression of Reaginic Antibody Formation IV. Suppression of Reaginic Antibodies to Penicillin in the Mouse", *The Journal of Immunology*, vol. 117, No. 3 (1976) pp. 927-934.

Old, R.W. et al., "Principles of Gene Manipulation An Introduction to Genetic Engineering", *Studies in Microbiology*, vol. 2 (1981) pp. 104-105, 119-120.

Sultan, Y. et al., "Anti-Idiotypic Suppression of Autoantibodies to Factor VIII (Antihaemophilic Factor) by High-Dose Intravenous Gammaglobulin", *The Lancet*, (1984) pp. 765-768.

\* cited by examiner

PHARMACEUTICAL COMPOSITIONS CONTAINING ANTIGEN-ANTIBODY COMPLEXES AND USES THEREFOR

This application is a continuation of application Ser. No. 07/806,772, filed Dec. 11, 1991, now abandoned, which is a continuation of application Ser. No. 07/460,514, filed Jan. 3, 1990, now abandoned, which is a continuation-in-part of application Ser. No. 07/038,985, filed Apr. 16, 1987, now abandoned, which is a continuation-in-part of application Ser. No. 06/651,073, filed Sep. 17, 1984, now U.S. Pat. No. 4,740,371.

The present invention relates to pharmaceutical compositions containing antigen-antibody complexes and their use in the treatment of autoimmune diseases and the prevention and treatment of graft rejections, both resulting from immunologic reactions of the body's immune system.

The immune system normally distinguishes between the body's own components and invading foreign material, and provides suitable mechanisms for destroying or containing harmful foreign agents. In the case of autoimmune disease, the immune system fails to make the distinction between self and non-self determinants, resulting in an immunologic reaction against and damage or destruction of the body's own cells.

Human autoimmune diseases are classified into two categories, i.e., organ specific and non-organ specific disorders. Myasthenia gravis is a representative autoimmune disease of the first category and systemic lupus erythematosus is a representative autoimmune disease of the second category. Myasthenia gravis is a neuromuscular disease that causes extreme muscle weakness. Normally a nerve impulse causes the release of acetylcholine from vesicles in a motor end plate of a nerve. The acetylcholine so released diffuses across the neuromuscular junction and combines with acetylcholine receptors on adjoining muscle fiber. This event induces the migration of membrane ions with a depolarization wave initiating the electric signal, causing muscular contraction. In patients suffering myasthenia gravis, IgG antibodies to the receptor are believed to block the binding of the acetylcholine to the receptors, impairing neuromuscular transmission.

Patients suffering the disease variably respond to anticholinesterase drugs, thymectomy, immunosuppressive agents, and plasmapheresis. Anticholinesterase drugs are often used to treat mild cases of myasthenia that are confined to extraocular muscles, but these medications may produce pronounced weakness and other untoward side effects. Despite the radical nature of thymectomy, it is the preferred treatment for many young patients with progressive or relatively severe disease, any patient with generalized myasthenia and a relatively recent onset of symptoms, and some older males with thymoma. Glucocorticosteroids may be helpful in severe cases and are often preferred for any patient suffering generalized myasthenia. Glucocorticosteroid treatment typically evokes an early transient worsening followed by gradual improvement. However, chronic glucocorticoid treatment can independently produce muscle weakness and wasting due to impaired muscle protein and carbohydrate metabolism. Also, resistance to infection is decreased because the immunosuppressive effects are generalized. Plasmapheresis, while effective in lowering antibody titers, often results in clinical improvement, but the results are temporary and reserved as a rescue procedure for severely affected patients that are resistant to other forms of therapy. With the possible exception of thymectomy, none of these conventional treatments attacks myasthenia at its cause, but instead merely alleviate disease symptoms.

Systemic lupus erythematosus (hereafter "SLE") is a multisystem disorder characterized by the presence of various autoantibodies that are responsible for immunopathologically mediated tissue injury. The pathogenic antibody in patients suffering SLE is directed against native double-strand DNA and extractable nuclear antigens (hereafter "ENA").

Conventional treatment of SLE takes various forms depending on the severity and type of organ involvement. Aspirin and other nonsteroidal anti-inflammatory agents alleviate symptoms manifest in mild forms of the disease, but may adversely affect hepatic and renal function. Corticosteroid therapy may alleviate acute exacerbations that involve vital organs, but high initial doses in the range of 40 to 100 milligrams per day of glucocorticoids (prednisolone) are usually required, and severe cases may require still higher dosages or prolonged treatment. Successful control of symptoms in recalcitrant, progressive renal or cerebral involvement usually requires continuous treatment with steroids and immunosuppressive drugs. Cytotoxic agents may be administered with steroids in more serious cases, but these agents have been known to cause serious side effects.

Conventional treatments of autoimmune diseases other than myasthenia gravis and SLE may similarly involve steroid therapy, immunosuppressive agents, and anti-inflammatory agents. As in the case of myasthenia gravis and SLE, these treatments, with the possible exception of thymectomy, suffer the inability to reach the source rather than the symptoms of the disease. These treatments are palliative and are not without adverse side effects. Ideally, treatment should be aimed at eliminating only the abnormal autoimmune response while leaving the ability to respond to other antigens intact.

The major immunologic complication of tissue transplantation from one person to another is rejection. Two factors largely determine the speed with which a graft is rejected: the degree of presensitization and the magnitude of mismatch between donor and recipient. Immediate hyperacute rejections result from preformed antibodies against the graft in the recipient's circulation. Such antibodies may result from ABO-incompatibility, prior transfusion grafting, or pregnancy. In highly sensitized patients, anti-HLA antibodies can be removed by plasma exchange and more recently by extracorporeal immunoadsorption with Staphylococcal protein A. But despite treatment with immunosuppressive drugs, antibody resynthesis remains a major problem. Acute rejections begin more than five days after the transplant and then proceed rapidly. Chronic rejection involves a gradual loss of function of a grafted organ.

Some graft reactions, especially immediate hyperacute reactions and chronic reactions, are irreversible or largely unresponsive to treatment. Prevention of such reactions thus becomes imperative. Several conventional methods for preventing graft reactions are known. Antigen matching is considered essential to help avoid hyperacute reactions of all but perhaps bone marrow grafts. Testing for presensitization is also important and is accomplished by determining the presence in the donor of complement dependent lymphocytotoxic antibodies, antibodies that mediate cellular cytotoxicity, and killer T-cells having reactivity against transplantation antigens of the donor. But antigen matching and presensitization testing prior to an allograft only decreases and does not eliminate the risk of rejection.

Immunosuppression techniques are often effective in further reducing the risk of rejection and may help arrest graft rejection once it occurs. Typical immunosuppression techniques in the case of renal transplantation involves the administration of corticosteroids such as methylprednisolone and prednisone and the administration of azathioprine for extended periods following transplantation. Blood transfusions from the donor may be prescribed, especially before renal transplantations. Lymphoid irradiation is used in renal transplantations to supplement immunosuppression measures when patients have already rejected renal transplants and are at risk for early rejection of subsequent grafts.

The successful transplantation of living tissue nevertheless remains a serious problem. A high percentage of rejections are unavoidable and unresponsive to conventional treatments. Extensive immunosuppressive therapy suppresses beneficial aspects of the immune system and may increase the risk of unrelated infection.

Additional background information may be found in Kohler et al., "The Autoimmune Diseases," Fink et al., "Immunological Aspects of Neurological and Neuromuscular Diseases," and Kirkpatrick et al., "Transplantation Immunology," Journal of the American Medical Association, Vol. 248, No. 20, pp. 2646–57, 2710–15 and 2727–33, Nov. 26, 1982, and Roitt et al., Immunology, copyright 1985 by Gower Medical Publishing Ltd., London. Further background is found in "Myasthenia Gravis," Lindstrom et al., *Advances in Immunology,* 1988, Vol. 42, pp. 233–284, "Immune Recognition of Antigen and Its Relevance to Autoimmune Disease: Recent Advances at the Molecular Level," *Eur. J. of Clin. Investigation,* 1989, Vol. 19, pp. 107–116, and "Organ Specific Autoimmunity: A 1986 Overview," *Immunological Reviews,* 1986, No. 94, pp. 136–169.

It is accordingly an object of the present invention to provide a pharmaceutical composition and method for the effective treatment of autoimmune diseases and the alleviation of related disease symptoms.

It is a further object of the invention to provide a pharmaceutical composition and method for altering the course of autoimmune diseases without producing undesired side effects.

It is a further object of the invention to provide a pharmaceutical composition and method for treating autoimmune diseases without surgery.

It is a further object of the invention to provide a pharmaceutical composition and method for treating autoimmune diseases that effect a steady and relatively rapid and permanent improvement of the disease symptomatology.

It is a further object of the invention to provide a pharmaceutical composition and method for preventing graft reactions.

It is a further object of the invention to provide a pharmaceutical composition and method for treating graft rejections.

It is a further object of the invention to provide a pharmaceutical composition and method for lowering the level of antibodies involved in a graft rejection without suppressing the entire immune system.

Other objects of the present invention will be apparent from the foregoing detailed description.

SUMMARY OF THE INVENTION

The present invention satisfies these objects by providing pharmaceutical compositions containing immune complexes of antigens and purified antibodies specific thereto, and physiologically acceptable carriers or diluents. The antigens are selected from a group of antigens that cause immunologic reactions associated with autoimmune diseases and graft rejections. The antigens and antibodies are present in a ratio in which essentially all binding sites of said antigen are blocked by said antibody, such that the antigens produce essentially no immunologic reaction when administered to the patient. The compositions are administered to treat the autoimmune diseases and to prevent or treat the graft rejections.

DETAILED DESCRIPTION OF THE PREFERRED EMBODIMENTS

The present invention provides numerous advantages over conventional methods for the treatment of autoimmune disease. First, it is believed to be universal to all autoimmune disease, thus delivering a versatile and effective tool in the treatment of many disorders. Autoimmune diseases which have previously been largely but not completely controlled by conventional techniques are now better and more safely and conveniently treated with the present invention. Patients suffering more serious autoimmune diseases which in the past have largely been unresponsive to conventional treatments now find relief under treatment with the present invention.

Second, the invention is simply and easily practiced. The effective ingredient of the composition is an immune complex of the antigen that evokes an immunologic response associated with the disease and the antibody directed against that antigen. Antigens have been identified for many autoimmune diseases and these antigens are sometimes commercially available. In these cases, the immune complex of the present invention is readily made by preparing or isolating and purifying antibody to those antigens and mixing the antigen and antibody in selected ratios. For other autoimmune diseases where associated antigens have been identified but are not commercially available, preparation of the immune complex requires the additional steps of isolating and purifying, synthesizing, or genetically engineering the antigen in accordance with techniques known in the art. For still other autoimmune diseases for which the pathogenic antigen has not been identified, the fruits of the invention are available upon the discovery of the causative antigen.

Third, the inventive composition by its nature causes little if any toxicity. The immune complex in a preferred embodiment is formed of antigen and antibody identical to that which is already present in the patient. Other components of the composition are pharmacologically compatible and may otherwise be varied with considerable latitude to avoid any possible adverse reaction that might be specific to a particular individual. The simplicity and largely indigenous nature of the composition also allows treatment in accord with the present invention to be combined safely and effectively with prior art therapies as may be beneficial.

Fourth, the invention avoids the many other disadvantages of conventional treatments, yet yields comparable or superlative results. Most fundamentally, the invention acts at the causative level and in many cases arrests the course of the disease. Successful treatment in accord with the invention allows much attenuated dosage levels in a relatively short period of time, and prospects for complete cure and the discontinuation of treatment in many cases are very good. The invention at the same time requires no radical procedures as in the case of organ removal or plasma exchanges, and does not suppress the body's immunologic defense to antigens unrelated to the disease. Still other advantages of the invention will be readily apparent to those skilled in the art.

The invention similarly provides numerous advantages over conventional techniques for the prevention or treatment of graft rejections. The invention is believed universally applicable to all types of immunologic reactions to grafts. The inventive composition is simply prepared as in the case of its use in treating autoimmune disease, the primary difference being in the selection of the antigen and respective antibody. The invention effectively prevents or treats graft rejections, yet avoids tissue damage and other disadvantages of conventional techniques.

The specific mode of action by which the present invention achieves its success is unknown, but it is hypothesized that the benefits flow from the occurrence of antigen-antibody immune complex which is inevitably present in the presently described mixtures of antigen and antibody. It is believed that the immune complexes stimulate the production of anti-idiotypic antibodies against the antibodies that are specific to the pathogenic antigen. The anti-idiotypic antibodies in turn suppress the production of the antibodies at the cellular or possibly the humoral level. This hypothesis is offered to allow a better understanding of the invention, but is not to be construed in any way to limit the scope of the appended claims.

All types of autoimmune disease, where target autoantigens are involved in the pathogenesis of both the non-organ specific and the organ-specific diseases, are treatable with the present invention. Organ specific diseases include myasthenia gravis, Addison's disease, thyroiditis, insulin-dependent and insulin-independent diabetes, Grave's disease, chronic atrophic gastritis, uveitis, multiple sclerosis, autoimmune hemolytic anemia, idiopathic thrombocytopenia purpura, Goodpasture's syndrome, some cases of male infertility, vitiligo and pemphigus. Organ non-specific diseases are systemic lupus erythematosus, scleroderma, Sjögren's disease, rheumatoid arthritis, and mixed connective tissue disease.

The antigen selected for the immune complex of the present invention causes a pathogenic immunologic reaction associated with the etiology of the autoimmune disease or graft rejection to be treated. For the treatment of any specific disorder, the composition typically includes a single causative antigen, but the composition includes multiple antigens, and respective multiple families of antibodies thereto, when a plurality of antigens are known to be pathogenically involved. The antigen is acetylcholine receptor (AChR) in the case of myasthenia, adrenal cell cytoplasm in the case of Addison's disease, thyroglobulin (Tg) and/or thyroid microsomal antigen (TMA) in the case of autoimmune thyroiditis, insulin receptor in the case of insulin resistant diabetes, islet cells and/or insulin in the case of insulin dependent diabetes, thyroid stimulating hormone receptor (TSH-R) in the case of Grave's disease, gastric cell microsomes in the case of atrophic gastritis, retinal S-antigen in the case of uveitis, myelin in the case of multiple sclerosis, red blood cell in the case of autoimmune hemolytic anemia, platelets in the case of idiopathic thrombocytopenia purpura, type IV collagen in the case of Goodpasture's syndrome, sperm in the case of male infertility, melanocytes in the case of vitiligo, and skin component in the case of pemphigus. The antigens are double stranded DNA and/or ENA in the case of lupus erythematosus, SS-A/Ro and SS-B/La in the case of Sjögren's syndrome, RNP in the of mixed connective tissue disease, Scl 70 and collagen-II or centromere in the case of scleroderma, and Fc region of IgG in the case of rheumatoid arthritis. The antigens involved in graft rejections are donor antigens, such as ABO and MHC class 1 and 2 antigens.

A number of the above-identified antigens are commercially available. These include: human thyroglobulin (Dako Corporation, Santa Barbara, Calif. 93103, Accurate Chemical and Scientific Corp., Westbury, N.Y. 11590); human collagen type IV (Southern Biotechnology Associates, Inc., Birmingham, Ala. 35226); human insulin (Peptides International, Louisville, Ky. 40223); and myelin basic protein (Chemicon International, Inc., El Segundo, Calif. 90245). Because the antibody will react only with its specific antigen, almost any preparation of antigen is suitable, even antigen in the form of crude extracts, provided it is devoid of toxic substances. However, the use of pure or relatively pure preparations of antigen is preferred because it is then easier to assess and control the amount of antigen present, which is important in controlling doses.

For many of the diseases to which the present invention is directed, only relatively impure antigen is readily available. Generally, such antigen may be purified for effective use in the invention by several techniques. In some cases, purification from human material is a viable approach, depending on the nature of the antigen itself. For example, material derived from biopsies or tissue samples (acetylcholine receptor or retinal S-antigen) would be difficult to use, whereas material derived from blood is practical and more suitable as a source (for example, platelet-derived proteins).

An alternative source of antigen that in some cases overcomes the practical difficulties involved in purification from human material is antigen derived from non-human material, such as AChR from electric eel. Immunological differences between antigen of human and non-human origin is not that significant in certain cases where animal antigens have high degrees of similarities with human counterparts. The practicality of this approach is increased by the fact that the antigen of the presently claimed invention is presented in the form of a complex, which is believed to reduce the immunogenicity of a non-human antigen.

Still other sources of sufficiently purified antigen exist. The increasingly precise identification of the nature of antigens involved in autoimmune diseases renders possible the production of such antigens by genetic engineering techniques and the like. Where precise knowledge of antigens is available, at least parts of a macromolecule, for example, particular epitopes, may be produced by chemical synthesis. Still another source of antigen may be the use of the internal image of antigen, since it is well known that anti-idiotypic antibodies can mimic certain epitopes of the original antigen. This approach has been used experimentally in the preparation of vaccines, where the antigen on its own represents a potential infective risk.

Specific examples of antigen preparation by genetic engineering and synthesis are known. The cloning of TSH—R, for example, is described in "Molecular Cloning of a cDNA Encoding a Human Thyrotropin Receptor," 8*th Int. Congress of Endocrinology,* 1988, Kyoto, Japan, p. 175, No. 04-22-052. Other techniques are applicable to antigens that carry a small number of antigenic determinants made of a small number of amino acids, usually 3 to 6. These antigenic determinants are synthesized in vitro and are usually coupled to a carrier protein with variable degrees of substitution. As an alternative, the antigenic determinants are purified and sequenced and the corresponding DNA sequence determined. This DNA is introduced in the genome of a microorganism which is used to synthesize the antigen in vitro. Additional references teaching suitable genetic engineering techniques include (1) T. Maniatis et al., *Molecular Cloning,* published 1982 by Cold Spring Harbor Laboratory, (2) B. Wallace et al., *Solid Phase Biochemistry,* page 631, published 1983 by J. Wiley & Sons, New York (edited by W. H. Scouten), and (3) K. Murray, *Philosophical Transactions of the Royal Society of London—Part B*, Vol. 290, pages 369–386 (1980). In still other specific embodiments, the antigen is chemically modified by glutaraldehyde, ethylene glycol derivatives or the like.

Causative antigens are believed to exist but are not yet positively identified for certain other autoimmune diseases. In these cases, the invention includes the additional preparatory step of identifying the antigen. The universal applicability of the present invention enables its straightforward implementation upon the discovery of heretofore unknown pathogenic antigens.

Once the antigen has been selected, an antibody thereto is obtained from three possible sources: (a) immunized animals, (b) individual blood donors and pooled plasma from multiple donors, and (c) the patient himself. It is preferred to use antibodies from the patient because the patient will normally have larger amounts of the specific antibodies required than will blood donors. On the other hand, the use of antibodies from pooled plasma is commercially desirable since it allows the preparation of pre-packaged antigen-antibody complexes without involving the patient. Antibodies of animal origin are generally the least desirable because of the risk of undesirable side reactions.

The antibody is polyclonal or monoclonal and is present in one embodiment in the form of either an Ig fraction or a more purified form such as $F(ab')_2$. The use of polyclonal antibodies decreases the risk of antigenic reactions against unmasked antigenic determinants. A method for preparing monoclonal antibodies is described in "Immunochemical Techniques—Part 1—Hybridoma Technology and Monoclonal Antibodies", *Methods in Enzymology*, Vol. 121, edited by J. J. Langone et al. and published in 1986 by Academic Press, Inc.

The antibody is preferably purified. Purification has the advantage of removing therapeutically irrelevant materials. The complexing of antigen with antibody in serum can result, among other things, in complement activation. Complement occurring on the surface of the antigen-antibody complex may interfere with the complex's intended in vivo behavior.

The antibody is suitably purified by various known techniques. One such technique involves specific absorption on the respective antigen which has been insolubilized by coupling to a solid phase. The antibody is then recovered by elution under conditions which dissociate the antigen-antibody complex, such as conditions of extreme pH, or by the use of chaotropic agents. The examples that follow illustrate these techniques.

Compositions of the invention are made by mixing the antigen or antigens with the respective antibody or antibodies in a form suited to the particular mode of administration that is selected. The ratio of antigen to antibody depends largely on the size of the antigen, since the number of antigenic determinants on the antigen is in general proportional to the molecular weight of the antigen. Sufficient antibody must be used to block essentially all of the available binding sites of the antigen, so that there is practically no antigenic effect by the antigen when the composition is administered. The minimum amount of antibody is normally a molar equivalent for reaction with the antigen, and the antibody is preferably present in a molar excess. If desired, routine testing reveals for any particular antigen and antibody the minimum amount of antibody to be used. There is no maximum to the amount of antibody, but for safety, a molar excess of up to about 500 is used. An even larger antibody excess can be used but is wasteful of the valuable material. Thus, a suitable antigen-to-antibody molar ratio ranges from 1:1 to 1:500, and preferably from at least about 1:3 to 1:500.

One simple method of preparing the mixture of antigen and antibody, which avoids the necessity of purifying the antigen or the antibody, is the use of the immune precipitate. In one embodiment, the precipitate is prepared by incubating a crude preparation of immunoglobulin from the patient's plasma or serum with the antigen and then centrifuging. The precipitation process is enhanced by the addition of polymers such as polyethylene glycol and dextran, or biological reagents such as rheumatoid factor or the Clq factor of complement. These techniques are well known and are illustrated in the examples that follow.

The compositions of the invention contain other components in addition to the antigen and antibody. In the case of injectables, suitable additional components include human albumin to prevent denaturation of antibody, antiseptic agents such as phenol, and adjuvants such as peptidoglycans and tyrosine crystals.

Suitable liquid carriers for the composition when in injectable form include distilled water, or more preferably saline or buffered saline. In preferred embodiments, the composition includes a saline carrier of 9 grams per liter of sodium chloride, or a buffered saline carrier having a pH of 7.4. Suitable liquid carriers are of low irritance, e.g., of neutral pH and physiological ionic strength. The selection of other pharmacologically acceptable carriers and diluents for use in the compositions is within the skill of those ordinarily skilled in the art.

The compositions of the invention are prepared in a variety of forms depending on the manner of administration. They are suitably prepared in a sterile injectable form, slow-release implant form, a form appropriate for local application to nasal, bronchial, lacrimal and/or gastrointestinal mucosae, in which case they are suitably in an aerosol or spray form or in a form similar to eye or nose drops, or as protected enteric capsules or the like. Other suitable forms will be readily apparent to those ordinarily skilled in the art.

When the compositions are prepared in liquid form, the liquids are suitably solutions or suspensions. The liquids are stored in ampules or are lyophilized and reconstituted immediately prior to use. The compositions of the invention are fairly stable, and in sterile ampules, can normally be stored at 4° C. for a limited time, or at −20° C. for 12 to 24 months. When lyophilized, their storage life is much longer.

The injectable compositions of the invention are injected intradermally, subcutaneously, intramuscularly, and with great care, intravenously. The intradermal route is preferred because it may cause a very clear skin reaction if insufficient antibody is present to neutralize the antigen. The frequency of injections varies very widely, for example, from daily to yearly, depending upon the antigen, the severity of the disease, and the stage of treatment.

The strength of the compositions is preferably expressed in terms of the antigen concentration and the antigen-to-antibody ratio. A suitable dosage range for the antigen is from about 1 nanogram to about 100 micrograms, and the antigen-to-antibody ratio is selected to mask the antigen's antigenicity. The initial antigen dosage is preferably relatively small, a precautionary measure against unexpected adverse reactions, and is then increased in subsequent administrations to a more effective level. Treatment efficacy is monitored by estimating antibody level against autoantigens and clinical patient status in the case of autoimmune diseases. Treatment efficacy is monitored by estimating anti-ABO or HLA titers and observing indicia of graft rejection in the case of transplantation. It is possible that a threshold dose of antigen-antibody complexes must be reached before a clinical improvement can be noted.

It will be readily apparent to those skilled in the art that modifications to the presently described techniques of preparation may be appropriate in the practice of the present invention and are within the scope of the invention as claimed. In order that the invention may be more fully understood, the following examples illustrate how it is made and used.

EXAMPLE 1

Preparation and Use of Compositions for the Treatment of Myasthenia Gravis

Due to the extremely low amounts of receptor available from human tissue, purification of the neuromuscular AChR is made from the electric organ of eels (*Torpedo marmorata*). Freshly thawed electric organ (200 g) is chopped and homogenized in 200 ml of 10 mM phosphate buffer containing 10 mM EDTA, 0.1 mM phenylmethylsulfonyl fluoride and 0.01% sodium azide, pH 7.4 (buffer A). The homogenate is centrifuged at 20.000×g for 1 hour and the pellet extracted with 200 ml of buffer A containing 1% (v/v) Triton X-100 at 4° C. for 16 hours. The extract is centrifuged at 100.000×g for 1 hour and the supernatant retained. Extract (100 ml) is applied to 50 ml of affinity resin, prepared by immobilizing 25 mg-cobratoxin on sepharose CL-4B with cyanogen bromide.

After 2 hours at 20° C., the beads are washed with buffer A containing 0.1% Triton X-100 (buffer B) and 1 mM NaCl and buffer B alone. The beads are then eluted with 20 ml of 1M Carbachol (Sigma, St. Louis, Mo.) in buffer B for 5 hours at 20° C.

After centrifugation, the supernatant is dialyzed overnight at 4° C. against 2 L of buffer B without EDTA (buffer C). It is then applied to a 2 ml column of DEAE cellulose (Whatman DE52, Maidstone, Kent) previously equilibrated with buffer C. The column is washed with 1 L of buffer C, and receptor is eluted using buffer C containing 0.5M NaCl. One-ml fractions are collected. (See *Eur. J. Immunol.* 1982, Vol. 12, pp. 757–761, Barkas T. et al.)

This preparation can be used for the isolation of specific anti-AChR antibodies; recombinant antigen would nevertheless be more appropriate for the immune complexes to be injected. See "Mapping of the Main Immunogenic Region and Toxin Binding Site of the Nicotinic Acetylcholine Receptor", Barkas et al., *Science,* 1988, Vol. 235, pp. 77–80.

One hundred ml of serum from a patient suffering myasthenia gravis are precipitated by the addition of 100 ml of 36 g/l $Na_2SO_4$, resuspended in phosphate buffered saline (PBS), and extensively dialyzed against the same buffer. The solution, which contains all immunoglobulins, is then passed through a TSK 55 gel filtration column (manufactured by E. Merck AG, Darmstadt, West Germany) to separate IgG from IgM. The IgG-containing fractions are pooled, concentrated by ultrafiltration to about 20 ml, and dialyzed against PBS. The IgG fraction is then passed over a Sepharose coated with Torpedo fish neuromuscular receptor, the column is washed thoroughly, and the adsorbed antibodies are recovered by elution with 50 mM citric acid of pH 2.6. The pH is then immediately restored to 7.4 and the solution is concentrated to 2 to 5 ml, dialyzed against PBS, and stored at −20° C. until use. The antigen is mixed in a 1:10 weight ratio with the specific antibodies isolated from a single patient. The mixture of antigen and antibodies is inoculated intradermally.

Having illustrated the practice of the invention in connection with several specific embodiments, those of ordinary skill in the art are taught to vary the elements of the invention, such as antigen dosage, antigen-antibody ratio, carrier or diluent, additives, preparatory techniques, and manner and periodicity of administration as may be appropriate to treat autoimmune disease and prevent or treat rejection reactions. It will be readily apparent to those skilled in the art that these and other modifications are within the spirit and scope of the present invention.

The invention claimed is:

1. A pharmaceutical composition suitable for administration to a human patient for mitigating a disease condition that is characterized by the pathological production of at least one specie of specific antibody by the patient, said disease being systemic lupus erythematosus, wherein said composition comprises:

an immune complex of an antigen and purified antibody specific thereto, said antigen being selected from the group consisting of antigens that are targeted by antibodies in immunologic reactions characteristic of said autoimmune disease, said purified antibody comprising at least one specie of specific antibody that is essentially identical to said at least one specie of specific antibody pathologically produced by the patient, and said antigen and said purified antibody being present in a ratio such that said purified antibody blocks essentially all binding sites of said antigen; and a pharmacologically acceptable carrier or diluent.

2. The composition of claim 1 wherein said antibody is human-derived.

3. The composition of claim 2 wherein said antibody is derived from pooled plasma from multiple donors.

4. The composition of claim 1 wherein said composition is prepared by a process comprising the steps of removing said antibody from human plasma, purifying said antibody, and mixing said purified antibody with said antigen.

5. The composition of claim 1 wherein said antibody is present, relative to said antigen, in a molar excess.

6. The composition of claim 1 wherein the antigen-to-antibody molar ratio is from about 1:1 to about 1:500.

7. The composition of claim 6 wherein the antigen-to-antibody molar ratio is at least about 1:3 to about 1:5000.

8. The composition of claim 1 wherein the antigen is present in a dose of from about 1 nanogram to about 100 micrograms.

9. The composition of claim 1 wherein said carrier or diluent is of approximately neutral pH.

10. The composition of claim 9 wherein said carrier is a liquid and said composition is in a sterile injectable form.

11. The composition of claim 10 wherein said liquid is saline.

12. The composition of claim 1 wherein said composition is in the form of a slow-release implant, a spray, an aerosol, drops or oral dose.

13. The composition of claim 1 wherein said composition is in lyophilized form.

14. The composition of claim 1 further comprising two or more antigens and two or more respective antibodies thereto.

15. A method for mitigating a disease condition of a human patient that is characterized by the pathological production of at least one specie of specific antibody by the patient, said disease being systemic lupus erythematosus, said method comprising the steps of:

selecting a pharmaceutical composition suitable for administration to said patient that comprises an immune complex of an antigen and purified antibody specific thereto, said antigen being selected from the group consisting of antigens that react in immunologic reactions with antibodies characteristic of said autoimmune disease, said purified antibody comprising at least one specie of specific antibody that is essentially identical to said at least one specie of specific antibody pathologically produced by the patient, and said antigen and said purified antibody being present in a ratio such that said purified antibody blocks essentially all binding sites of said antigen, and a pharmacologically acceptable carrier or diluent; and administering said composition to said patient.

16. The method of claim 15 further comprising the step of deriving said antibody from said patient.

17. The method of claim 15 further comprising the step of deriving said antibody from a pooled plasma from multiple donors.

18. The method of claim 15 wherein said step of administering comprises the step of injecting said composition.

19. The method of claim 15 wherein said step of administering comprises administering said composition in the form of an aerosol, enteric capsule, or drops of a viscous liquid.

20. The composition of claim 1 wherein the autoimmune disease is systemic lupus erythematosus and the antigen is double-stranded DNA and/or extractable nuclear antigens.

21. The method of claim 15 wherein the autoimmune disease is systemic lupus erythematosus and the antigen is double-stranded DNA and/or extractable nuclear antigens.

22. The composition of claim 1, wherein said purified antibody is polyclonal.

23. The method of claim 15, wherein said purified antibody is polyclonal.

24. The composition of claim 1 wherein said disease condition is mitigated upon a down-regulation of said at least one specie of specific antibody pathologically produced by the patient.

25. The composition of claim 1 wherein said purified antibody comprises a plurality of species of said specific antibodies that are essentially identical, respectively, to a plurality of species of specific antibodies pathologically produced by the patient.

26. The composition of claim 25 wherein said species of said specific antibodies of said purified antibody are, respectively, essentially identical to substantially all of said species of specific antibodies pathologically produced by the patient.

27. The composition of claim 25 or 26 wherein said purified antibody is polyclonal.

28. The method of claim 15 wherein said disease condition is mitigated upon a down-regulation of said at least one specie of specific antibody pathologically produced by the patient, and wherein said administering step causes such a down-regulation.

29. The method of claim 15 wherein said purified antibody comprises a plurality of species of said specific antibodies that are essentially identical, respectively, to a plurality of species of specific antibodies pathologically produced by the patient.

30. The method of claim 29 wherein said species of said specific antibodies of said purified antibody are, respectively, essentially identical to substantially all of said species of specific antibodies pathologically produced by the patient.

31. The method of claim 29 or 30 wherein said purified antibody is polyclonal.

* * * * *